US00PP28236P3

(12) United States Plant Patent
Marin

(10) Patent No.: US PP28,236 P3
(45) Date of Patent: Aug. 1, 2017

(54) LEMON TREE NAMED 'SUMMER PRIM'

(50) Latin Name: ***Citrus limon* (L.)**
Varietal Denomination: Summer Prim

(71) Applicant: Juan Antonio Gómez Marin, Murcia (ES)

(72) Inventor: Juan Antonio Gómez Marin, Murcia (ES)

( * ) Notice: Subject to any disclaimer, the term of this patent is extended or adjusted under 35 U.S.C. 154(b) by 44 days.

(21) Appl. No.: 14/545,406

(22) Filed: May 1, 2015

(65) Prior Publication Data

US 2015/0342102 P1 Nov. 26, 2015

(30) Foreign Application Priority Data

May 20, 2014 (ES) ..... PBR 20145150

(51) Int. Cl.
*A01H 5/08* (2006.01)

(52) U.S. Cl.
USPC ..... Plt./201

(58) Field of Classification Search
USPC ..... Plt./201
See application file for complete search history.

*Primary Examiner* — Keith Robinson
(74) *Attorney, Agent, or Firm* — Buchanan Ingersoll & Rooney PC

(57) ABSTRACT

A new and distinct cultivar *Citrus limon* (L.) Brum.f. is provided which displays a substantially different time for initial fruit harvest than the standard 'Primofiori' cultivar (non-patented in the United States). The attractive juicy fruit of the new cultivar commonly is initially ready for harvest by about the end of March. This follows greatly the typical October initial harvest time for the 'Primofiori' cultivar. The new cultivar is a diploid, and displays a relatively dense spreading growth habit. The supply of the fresh fruit market for consumption, use in beverages, and in cooking is facilitated at an atypical season of the year by the new cultivar.

4 Drawing Sheets

Botanical/commercial classification: *Citrus limon* (L.) Brum.f./Lemon Tree.

Varietal denomination: cv. 'Summer Prim'.

SUMMARY OF THE INVENTION

The new and distinct late-ripening lemon cultivar of the present invention was discovered while growing in a cultivated area of the Murica region of Spain while present among standard 'Primofiori' lemon trees (non-patented). A single plant of the new cultivar was found, was carefully preserved, and thereafter was observed to confirm its distinctive combination of characteristics. Had the new cultivar of the present invention not been discovered and preserved it would have been lost to mankind. This new cultivar is believed to be a spontaneous mutation of the 'Primofiori' lemon tree of unknown causation.

It was found that the new Lemon cultivar of the present invention:

(a) is a diploid, (b) forms attractive fruit which when compared to the 'Primofiori' cultivar displays a substantially later season of maturity, and, (c) displays a relatively dense spreading growth habit.

The new cultivar has been asexually reproduced at the Murcia region of Spain by grafting on standard 'sour orange' rootstock (non-patented). The combination of characteristics, including the consistent production of late maturing fruit, has been shown to be stable and is reliably transmitted to succeeding generations following such asexual reproduction. Accordingly, the new cultivar reproduces in a true-to-type manner by such asexual reproduction.

The fruit quality of the new cultivar has been found to be substantially similar to that of the standard 'Primofiori' cultivar.

The new cultivar can be readily distinguished from 'Primofiori' lemon in view of its extremely later time for the harvest of mature fruit. For instance, at the Murcia region of Spain the fruit of the 'Primofiori' lemon commonly is initially of a maturity suitable for harvest in October. However, the fruit of the new cultivar commonly is of a maturity suitable for harvest approximately six months later (i.e., during the following middle of May) when grown under comparable conditions in the Northern Hemisphere. Harvest commonly is carried out from about the end of March until about early-July.

Accordingly, growers of the new cultivar are able to supply the commercial market with quality freshly-picked lemon fruit at a different season of the year than growers of the 'Primofiori' lemon. The time of initial fruit maturity for new cultivar is displayed at a different time when fresh lemons continue to be in demand for purchase by consumers. Growers of the new cultivar thereby are enabled to benefit significantly from the atypical season of fruit maturity that is reliably manifest by the presently-claimed new lemon plant. It follows that those growing the standard 'Primofiori' lemon are unlikely to be able to offer quality freshly-picked mature fruit at the same time of the year.

The new plant of the present invention has been named 'Summer Prim'.

BRIEF DESCRIPTION OF THE PHOTOGRAPHS

The accompanying photographs show, as nearly true as is reasonably possible to make the same in color illustrations of this character, a typical tree of the new cultivar, as well as a comparison of the whole and sectioned fruit of the new cultivar with that of the 'Primofiori' and 'Verna' cultivars (each non-patented). The illustrated plants were grown under the same conditions at the Murcia region of Spain.

Figure 4:
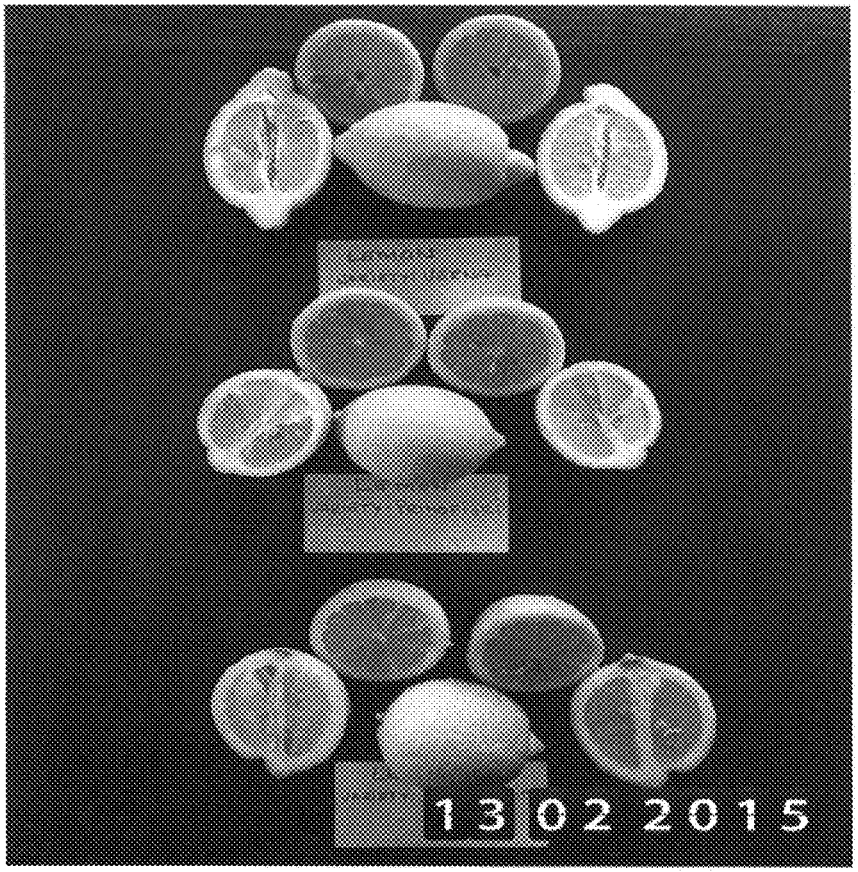

FIG. 4 shows for comparative purposes typical whole and sectioned fruit of the 'Verna' cultivar (top), the 'Primofiori' cultivar (middle), and the new cultivar of the present invention (bottom). The photograph was obtained on Feb. 13, 2015 at a time when the fruit of the new cultivar had not yet ripened to a stage of full maturity. The illustrated fruit of each cultivar was picked on the same date and was produced in the same field.

DETAILED BOTANICAL DESCRIPTION

The described plants of the new cultivar were approximately seven years of age, had been asexually reproduced by grafting on standard 'sour orange' rootstock (non-patented) outdoors in full sunlight at the Murcia region of Spain. Observations obtained during the growing season of 2014 are presented. All colors listed below are with reference to The Royal Horticulture Society (R.H.S.) Colour Chart (1995 Edition).

Classification: *Citrus limon* (L.) Burm.f.

Tree:

*Ploidy*.—Diploid.

*Growth habit*.—Dense and spreading.

*Spines*.—Relatively short, commonly approximately 6 mm in length on average, and commonly present in a moderate quantity.

Foliage:

*Leaf shape*.—Generally ovate to elliptic.

*Leaf apex*.—Acute with the absence of emargination.

*Leaf base*.—Substantially obtuse.

Figure 1:
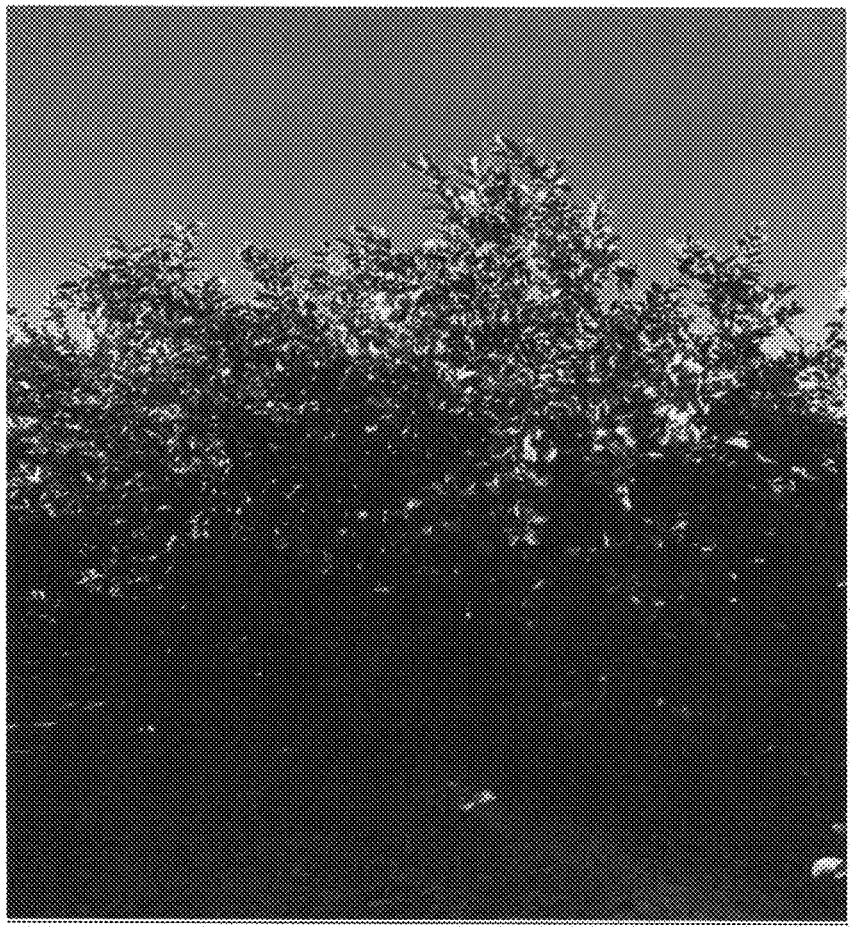
FIG. 1 shows the overall relatively dense and spreading growth habit of a typical specimen of the new cultivar. The photograph depicts a tree of approximately seven years of age and was obtained during March 2015.
Figure 2:
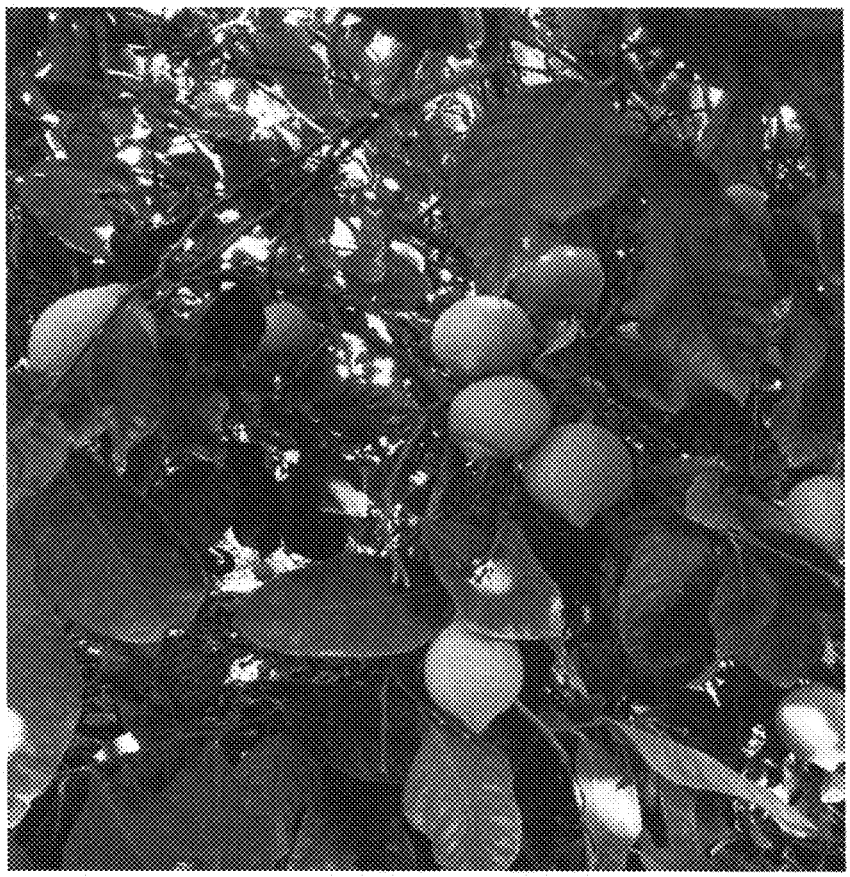
FIG. 2 shows a closer view of the foliage and the abundant formation of immature fruit that is in process of ripening while present on a typical specimen of the new cultivar. The same or a comparable tree to that of FIG. 1 is being depicted.
Figure 3:
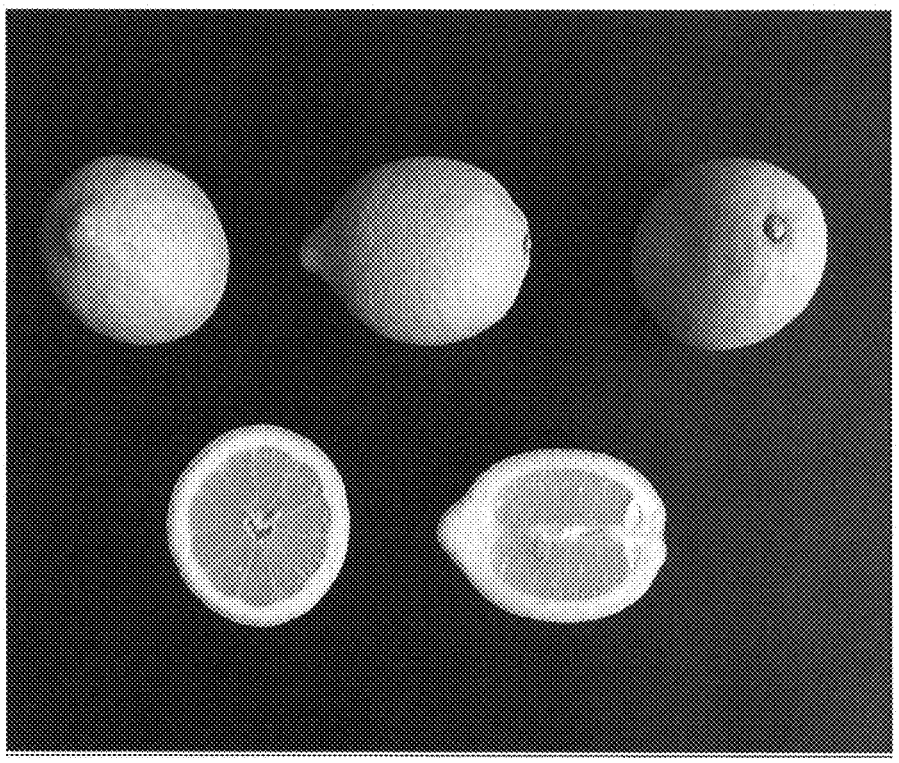
FIG. 3 shows whole and in cross sections attractive typical specimens of the mature fruit of the new cultivar of the invention at the time of harvest (i.e., typically during middle of May).

*Leaf size*.—Relatively long and broad, commonly approximately 103 mm in length and 52 mm in width on average, as illustrated in FIG. 2, and commonly intermediate in thickness.

*Leaf margin*.—Entire with absent or weak undulation.

*Leaf color*.—Commonly medium green, commonly near Green Group 143B on the upper surface and near Green Group 145 on the lower surface, with a moderate presence of anthocyanin.

*Petioles*.—Commonly approximately 12 mm in length and 3 mm in width on average with the absence of wings; color is commonly near Green Group N144D; texture is generally smooth.

Inflorescence:

*Habit*.—Commonly flowers once per season.

*Buds*.—Commonly approximately 2.4 mm in length and 1.1 mm in diameter on average; commonly near Green Group 144 in color with a moderate presentation of anthocyanin coloration; texture is generally smooth.

*Flower size*.—Medium in overall size, commonly approximately 23 mm in diameter and 18 mm in length on average.

*Petals*.—Commonly approximately 17.1 mm in length and 5 mm in width on average; commonly near Cream Group NN155D on the upper surface and near Cream Group NN155D blended with near Purple Group 84D on the lower surface; generally smooth in texture.

*Stamen*.—Generally 14-20 stamens per flower; overall stamen length is approximately 11.2 mm on average; filaments are commonly approximately 8.5 mm in length, and commonly near White Group 155C in color; anthers are cuneiform in shape, commonly approximately 2.7 mm in length and 1.4 mm in width, commonly light-yellow in coloration, near Yellow Group 8C and commonly bear abundant amounts of pollen of light-yellow coloration, commonly near Yellow Group 13C.

*Pistils*.—One per flower, commonly approximately 12.5 mm in length on average.

*Stigma*.—Generally spheroid in shape and commonly near Yellow Group 1B in color.

*Styles*.—Commonly approximately 6.5 mm in length on average in length, and commonly near Yellow Group 1B in color.

*Ovary*.—Commonly near Green Group 144A in color.

Fruit:

*Configuration*.—Generally elongated, relatively large in diameter and broadest towards the middle region (as illustrated); a depression is absent from the stalk end of the fruit; parthenocarpy is present.

*Size*.—Commonly approximately 75 mm in length and 58 mm in diameter.

*Neck*.—Absent.

*Proximal end*.—Slightly rounded.

*Distal end*.—Slightly rounded with the absence of grooves.

*Nipple*.—Commonly present and medium in size, approximately 12 mm in length and 5 mm in width on average.

*Surface texture*.—Generally smooth in the absence of extreme roughness, and commonly with moderate glossiness.

*Persistence of style*.—Commonly none.

*Rind*.—Commonly medium in thickness with medium oiliness.

*Surface color*.—Commonly near Yellow Green Group 150D in the substantial absence of variegation.

*Flesh color*.—Commonly near Yellow Group 8C.

*Filling of interior*.—Very dense commonly with a moderate number of developed segments and the absence of rudimentary segments.

*Core diameter*.—Relatively small, approximately 5 mm in diameter, on average.

*Seeds*.—Commonly approximately 6 to 10 per fruit on average; commonly approximately 4 mm in length and 3 mm in width on average; smooth in texture and commonly near Yellow Group 11D in color; seed is monoembryonic.

*Juiciness*.—High.

*Maturity*.—Commonly approximately 100 days to maturity on average.

*Harvest time*.—Commonly from about the end of March until about early-July in the northern Hemisphere.

*Market*.—Fresh for consumption, use in beverages, and for use in cooking.

Plants of the new 'Summer Prim' cultivar have not been observed under all possible environment conditions to date. Accordingly, it is possible that the phenotypic expression may vary somewhat with changes in light intensity and duration, cultural practices, and other environmental conditions.

I claim:

1. A new and distinct cultivar of lemon tree having the following combination of characteristics:

(a) displays diploidy, (b) forms attractive fruit which when compared to the 'Primofiori' cultivar displays a substantially later season of maturity, and (c) displays a relatively dense spreading growth habit; substantially as illustrated and described.

* * * * *